(12) United States Patent
Hardy et al.

US010188112B2

(10) Patent No.: US 10,188,112 B2
(45) Date of Patent: *Jan. 29, 2019

(54) PERSONAL CLEANSING COMPOSITIONS CONTAINING ZINC AMINO ACID/TRIMETHYLGLYCINE HALIDE

(71) Applicant: Colgate-Palmolive Company, New York, NY (US)

(72) Inventors: Eugene Hardy, Old Bridge, NJ (US); Long Pan, Cherry Hill, NJ (US); Shiri Nawrocki, Tenafly, NJ (US); Evangelia Arvanitidou, Princeton, NJ (US); Laurence D. Du-Thumm, Princeton, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/650,952

(22) PCT Filed: Nov. 20, 2013

(86) PCT No.: PCT/US2013/070932
§ 371 (c)(1),
(2) Date: Jun. 10, 2015

(87) PCT Pub. No.: WO2014/099226
PCT Pub. Date: Jun. 26, 2014

(65) Prior Publication Data
US 2015/0313827 A1 Nov. 5, 2015

Related U.S. Application Data

(63) Continuation-in-part of application No. PCT/US2012/070489, filed on Dec. 19, 2012, which is a continuation-in-part of application No. PCT/US2012/070492, filed on Dec. 19, 2012, which is a continuation-in-part of application No. PCT/US2012/070498, filed on Dec. 19, 2012, which is a continuation-in-part of application No. PCT/US2012/070501, filed on Dec. 19, 2012, which is a continuation-in-part of application No. PCT/US2012/070505, filed on Dec. 19, 2012, which is a continuation-in-part of application No. PCT/US2012/070506, filed on Dec. 19, 2012, which is a continuation-in-part of application No. PCT/US2012/070513, filed on Dec. 19, 2012, which is a continuation-in-part of application No. PCT/US2012/070521, filed on Dec. 19, 2012, which is a continuation-in-part of application No. PCT/US2012/070525, filed on Dec. 19, 2012, which is a continuation-in-part of application No. PCT/US2012/070534, filed on Dec. 19, 2012, which is a continuation-in-part of application No. PCT/US2012/070537, filed on Dec. 19, 2012, said application No. PCT/US2013/070932 is a continuation-in-part of application No. PCT/US2013/046268, filed on Jun. 18, 2013, and a continuation-in-part of application No. PCT/US2013/050845, filed on Jul. 17, 2013, and a
(Continued)

(51) Int. Cl.
| | | |
|---|---|---|
| A61K 8/58 | (2006.01) |
| A61Q 19/10 | (2006.01) |
| A61Q 15/00 | (2006.01) |
| A61Q 17/04 | (2006.01) |
| A01N 55/02 | (2006.01) |
| A01N 59/16 | (2006.01) |
| A61K 8/27 | (2006.01) |
| A61K 8/44 | (2006.01) |
| A61K 8/20 | (2006.01) |

(52) U.S. Cl.
CPC .............. *A01N 59/16* (2013.01); *A01N 55/02* (2013.01); *A61K 8/20* (2013.01); *A61K 8/27* (2013.01); *A61K 8/44* (2013.01); *A61K 8/58* (2013.01); *A61Q 15/00* (2013.01); *A61Q 17/04* (2013.01); *A61Q 19/10* (2013.01); *A61K 2800/58* (2013.01); *A61K 2800/592* (2013.01)

(58) Field of Classification Search
None
See application file for complete search history.

(56) References Cited

U.S. PATENT DOCUMENTS 2,503,280 A 4/1950 Lockwood
2,507,088 A 5/1950 Bradley
(Continued)

FOREIGN PATENT DOCUMENTS

CN 101172956 A * 5/2008
CN 101606639 12/2009
(Continued)

OTHER PUBLICATIONS

Translation of CN 101172956 A from Google and Espacenet.*
(Continued)

*Primary Examiner* — Michael P Cohen

(57) ABSTRACT

Provided is a personal cleansing composition for application to the skin which comprises a zinc X halide present in an amount to provide at least 0.36 weight % of the composition of zinc, and a surfactant, wherein X is an amino acid or trimethylglycine. Methods of making and using the compositions are also provided. The zinc X halide is can be used to deliver zinc salts to reduce or prevent sunburn, kill bacteria, or reduce perspiration.

19 Claims, No Drawings

Related U.S. Application Data continuation-in-part of application No. PCT/US2013/068852, filed on Nov. 7, 2013, which is a continuation-in-part of application No. PCT/US2013/068860, filed on Nov. 7, 2013, said application No. PCT/US2013/070932 is a continuation-in-part of application No. PCT/US2013/068859, filed on Nov. 7, 2013, and a continuation-in-part of application No. PCT/US2013/068854, filed on Nov. 7, 2013.

(56) References Cited

U.S. PATENT DOCUMENTS

| | | |
|---|---|---|
| 2,527,686 A | 10/1950 | Sandberg |
| 2,893,918 A | 7/1959 | Abramson |
| 3,260,744 A | 7/1966 | Kenkichi |
| 3,320,174 A | 5/1967 | Rubinfeld |
| 3,372,188 A | 3/1968 | Terence |
| 3,535,421 A | 10/1970 | Briner |
| 3,538,230 A | 11/1970 | Morton |
| 3,678,154 A | 7/1972 | Briner |
| 3,741,911 A | 6/1973 | Shane |
| 3,862,307 A | 1/1975 | Giulio |
| 3,937,807 A | 2/1976 | Haefele |
| 3,941,818 A | 3/1976 | Abdel-Monem |
| 3,959,458 A | 5/1976 | Agricola et al. |
| 4,051,234 A | 9/1977 | Gieske et al. |
| 4,316,824 A | 2/1982 | Pancheri |
| 4,339,432 A * | 7/1982 | Ritchey .......... A61K 8/27 424/49 |
| 4,340,583 A | 7/1982 | Wason |
| 4,487,757 A | 12/1984 | Kiozpeoplou |
| 4,565,693 A | 1/1986 | Marschner |
| 4,599,152 A | 7/1986 | Ashmead |
| 4,684,528 A | 8/1987 | Godfrey |
| 4,687,663 A | 8/1987 | Schaeffer |
| 4,842,847 A | 6/1989 | Amjad |
| 4,866,161 A | 9/1989 | Sikes et al. |
| 4,885,155 A | 12/1989 | Parran, Jr. et al. |
| 5,004,597 A | 4/1991 | Majeti et al. |
| 5,061,815 A * | 10/1991 | Leu .......... C07F 1/005 426/74 |
| 5,156,845 A | 10/1992 | Grodberg |
| 5,188,821 A | 2/1993 | Gaffar et al. |
| 5,192,531 A | 3/1993 | Gaffar et al. |
| 5,504,055 A | 4/1996 | Hsu |
| 5,643,559 A | 7/1997 | Eigen et al. |
| 5,698,724 A | 12/1997 | Anderson et al. |
| 5,707,679 A | 1/1998 | Nelson |
| 5,714,447 A | 2/1998 | Jones et al. |
| 5,911,978 A | 6/1999 | Carr et al. |
| 5,993,784 A | 11/1999 | Hill |
| 6,121,315 A | 9/2000 | Nair et al. |
| 6,156,293 A | 12/2000 | Jutila et al. |
| 6,558,710 B1 * | 5/2003 | Godfrey .......... A61K 33/30 424/405 |
| 6,607,711 B2 | 8/2003 | Pedersen |
| 6,660,699 B2 | 12/2003 | Finucane et al. |
| 6,685,920 B2 | 2/2004 | Baig et al. |
| 6,969,510 B2 | 11/2005 | Holerca et al. |
| 7,279,456 B2 * | 10/2007 | Dufay .......... A61K 8/44 424/401 |
| 8,067,627 B2 | 11/2011 | Newsome et al. |
| 8,247,398 B2 | 8/2012 | Goel |
| 9,498,421 B2 * | 11/2016 | Liu .......... A61K 8/447 |
| 2004/0033916 A1 | 2/2004 | Kuzmin et al. |
| 2004/0042978 A1 | 3/2004 | Embro |
| 2004/0122088 A1 | 6/2004 | Newsome et al. |
| 2004/0198998 A1 | 10/2004 | Holerca et al. |
| 2006/0024252 A1 | 2/2006 | Esposito et al. |
| 2007/0071698 A1 * | 3/2007 | Doss .......... A61K 36/328 424/59 |
| 2009/0220444 A1 | 9/2009 | Teckenbrock et al. |
| 2010/0021573 A1 | 1/2010 | Gonzalez et al. |
| 2010/0266480 A1 | 10/2010 | Huang |
| 2010/0330163 A1 | 12/2010 | Soparkar |
| 2011/0076309 A1 | 3/2011 | Misner et al. |
| 2011/0229536 A1 | 9/2011 | Kvitnitsky et al. |
| 2013/0017240 A1 | 1/2013 | Porter et al. |
| 2014/0170086 A1 | 6/2014 | Pan et al. |

FOREIGN PATENT DOCUMENTS

| | | |
|---|---|---|
| CN | 102811698 | 12/2012 |
| CN | 103156073 | 6/2013 |
| CN | 103535536 | 1/2014 |
| DE | 735096 | 5/1943 |
| EP | 0083486 | 12/1982 |
| EP | 0108937 | 5/1984 |
| EP | 0508524 | 10/1992 |
| EP | 0514553 | 11/1992 |
| EP | 0842664 | 5/1998 |
| EP | 1021158 | 7/2000 |
| EP | 1064946 | 1/2001 |
| EP | 1203575 | 5/2002 |
| EP | 1319394 | 6/2003 |
| EP | 1935395 | 6/2008 |
| EP | 1529775 | 5/2011 |
| FR | 2241301 | 3/1975 |
| GB | 2052978 | 2/1981 |
| GB | 2109685 | 6/1983 |
| GB | 2243775 | 11/1991 |
| JP | S57-158724 | 9/1982 |
| JP | 2004175790 | 6/2004 |
| JP | 2009084201 | 4/2009 |
| JP | 2010132639 | 6/2010 |
| WO | WO86/00004 | 1/1986 |
| WO | WO9917735 | 4/1999 |
| WO | WO199917735 | 4/1999 |
| WO | WO0169087 | 9/2001 |
| WO | WO2004054531 | 7/2004 |
| WO | WO2004/064536 | 8/2004 |
| WO | WO2014204439 | 12/2004 |
| WO | WO2007063507 | 6/2007 |
| WO | WO2011053291 | 5/2011 |
| WO | WO2011/088199 | 7/2011 |
| WO | WO2011/123123 | 10/2011 |
| WO | WO2014/098813 | 6/2014 |
| WO | WO2014/098814 | 6/2014 |
| WO | WO2014/098818 | 6/2014 |
| WO | WO2014/098819 | 6/2014 |
| WO | WO2014/098821 | 6/2014 |
| WO | WO2014/098822 | 6/2014 |
| WO | WO2014/098824 | 6/2014 |
| WO | WO2014/099164 | 6/2014 |
| WO | WO2014/099165 | 6/2014 |
| WO | WO2014/099166 | 6/2014 |
| WO | WO2014/099167 | 6/2014 |
| WO | WO2014098825 | 6/2014 |
| WO | WO2014098826 | 6/2014 |
| WO | WO2014098828 | 6/2014 |
| WO | WO2014098829 | 6/2014 |
| WO | WO2014099039 | 6/2014 |
| WO | WO2014099226 | 6/2014 |

OTHER PUBLICATIONS

GP Dransfield. Inorganic Sunscreens. Radiation Protection Dosimetry. vol. 91, Nos. 1-3, 2000, pp. 271-271.*

Anonymous, "Zinc Lauryl Ether Sulphate, A New Approach to Skincare,", Apr. 2004, Retrieved from Internet, http://www.erwebhosting.it/zsi/repository/Zinc%20Lauryl%20Ether%20Sulphate,%20A%20new%20approach%20to%20skin%20care.pdf, Retrieved Sep. 26, 2013.

Deschaume et al., "Interactions of aluminum hydrolytic species with biomolecules," New Journal of Chemistry, 2008, 32:1346-1353.

European Food Safety Authority, "Scientific Opinion on the safety and efficacy of tetra-basic zinc chloride for all animal species," EFSA Journal, 2012, 10(5):2672.

Hartwell et al., "Preparation and characterization of tyrosine and lysine metal chelate polyesters and polyamides", J. of the American Chem. Society, Mar. 1970, 92(5): 1284-1289.

(56) References Cited

OTHER PUBLICATIONS

International Search Report and Written Opinion for International Application No. PCT/US2012/070489 dated Oct. 22, 2013.
International Search Report and Written Opinion for International Application No. PCT/US2012/070492 dated Oct. 22, 2013.
International Search Report and Written Opinion for International Application No. PCT/US2012/070498 dated Sep. 4, 2013.
International Search Report and Written Opinion for International Application No. PCT/US2012/070501 dated Oct. 21, 2013.
International Search Report and Written Opinion for International Application No. PCT/US2012/070505 dated Nov. 20, 2013.
International Search Report and Written Opinion for International Application No. PCT/US2012/070506 dated Oct. 14, 2013.
International Search Report and Written Opinion for International Application No. PCT/US2012/070513 dated Oct. 14, 2013.
International Search Report and Written Opinion for international Application No. PCT/US2012/070521 dated Sep. 30, 2013.
International Search Report and Written Opinion for International Application No. PCT/US2012/070525 dated Sep. 27, 2013.
International Search Report and Written Opinion for International Application No. PCT/US2012/070528 dated Sep. 30, 2013.
International Search Report and Written Opinion for International Application No. PCT/US2012/070534 dated Sep. 26, 2013.
International Search Report and Written Opinion for International Application No. PCT/US2012/070537 dated Oct. 11, 2013.
International Search Report and Written Opinion for International Application No. PCT/US2013/046268 dated Apr. 22, 2014.
International Search Report and Written Opinion for International Application No. PCT/US2013/050845 dated Aug. 13, 2014.
International Search Report and Written Opinion for International Application No. PCT/US2013/068852 dated Nov. 10, 2014.
International Search Report and Written Opinion for International Application No. PCT/US2013/068854 dated Oct. 20, 2014.
International Search Report and Written Opinion for International Application No. PCT/US2013/068859 dated Aug. 4, 2014.
International Search Report and Written Opinion for International Application No. PCT/US2013/068860 dated Oct. 22, 2014.
International Search Report and Written Opinion for International Application No. PCT/US2013/070932 dated Jul. 24, 2014.
International Search Report and Written Opinion for International Application No. PCT/US2014/042947 dated Aug. 22, 2014.
International Search Report and Written Opinion for International Application No. PCT/US2014/042948 dated Aug. 26, 2014.
International Search Report and Written Opinion for International Application No. PCT/US2014/043051 dated Feb. 18, 2015.
Kondrot, "The Importance of Zinc," http://www.healingtheeye.com/Articles/zinc.html, Feb. 21, 2012.
Liang et al., "In vitro scratch assay: a convenient and inexpensive method for analysis of cell migration in vitro," Nature Protocols, 2007, 2(2):329-333.
Liu et al., "The research on zinc coordination number 5 odd structure in zinc complex with L-lysine," J. Molecular Science, 2000, 16(2):114-117, abstract only in English.
Lu et al., "Albumin as a zinc carrier: properties of its high-affinity zinc-binding site". Biochem. Soc. Trans., 2008, 36:1317-1321.
Lynch, "Zinc in the mouth, its interactions with dental enamel and possible effects on caries: a review of the literature," Int. Dent. J., Aug. 2011, Suppl 3:46-54.

Mavromichalis et al., "Growth-promoting efficacy of pharmacological doses of tetrabasic zinc chloride in diets for nursery pigs," Canadian Journal of Animal Science, pp. 387-391, Jan. 2001.
McAuliffe et al., "Metal complexes of sulphur-containing amino acids," Inorganica Chimica Acta Reviews, Dec. 1972, 6:103-121.
Moore et al., "Antibacterial activity of gutta-percha cones attributed to the zinc oxide component," Oral Surgery, 1982, 53:508-517.
Mosmann, "Rapid colorimetric assay for cellular growth and survival: Application to proliferation and cytotoxicity assays," J. Immunol. Methods, 1983, 65:55-63.
Pashley et al. Dentin permeability effects of desensitizing dentifrices in vitro. J Periodontol. 1984;55(9):522-525.
Prasad, "Zinc:role in immunity, oxidative stress and chronic inflammation," Current Opinion in Clinical Nutrition and Metabolic Care, 2009, 12:646-652.
Rigano, L., Zinc Lauryl Ether Sulphate—A New Approach to Skin Care, SOFW Journal, Apr. 2004, 128:26-33.
Schmetzer et al., "Wulfingite, ε-Zn(OH)2, and simorikolleite, Zn5(OH)8Cl2•H2O, two new minerals from Richelsdorf, Hesse, F.R.G.," N. Jb. Miner. Mh., Apr. 1985, pp. 145-154.
Seil et al., "Antibacterial effect of zinc oxide nanoparticles combined with ultrasound," Nanotechology,2012, 23:495101.
Soderling et al., "Betaine-containing toothpaste relieves subjective symptoms of dry mouth," Acta Odontol. Scand., Apr. 1998, 56(2):65-9.
Stewart et al., "Interdomain zinc site on human albumin," PNAS, 2003, 100(7):3701-3706.
Tian et al., "Using DGGE profiling to develop a novel culture medium suitable for oral microbial communities," Molecular Oral Microbiology, 2010, 25(5):357-367.
Twetman et al., 2003, "Caries-preventative effect of fluoride toothpaste a systematic review," Acta Odontol Scand., Dec. 2003, 61(6):347-55.
Wachi et al., "Antibacterial compsn. Zinc oxide—solubilized by ammo acid, amino acid hydrochloride and/or amino acid alkali metal salt," Sep. 1982, vol. 1982(45).
Wallhausser et al., "Antimicrobial Preservatives in Europe: Experience with preservatives used in pharmaceuticals and cosmetics," Develop. Biol. Standard, 1974, 24:9-28.
Yao et al., "An investigation of zirconium(IV)-glycine(CP-2) hybrid complex in bovine serum albumin protein matrix under varying conditions," J. of Materials Chemistry, 2011, 21:19005-19012.
Yousef et al., "In Nitro antibacterial activity and minimum inhibitory concentration of zinc oxide and nano-particle zinc oxide against pathogenic strains," J. of Health Sciences, 2012, 2(4):38-42.
Zhu et al., "Synthesis and Crystal Structure of [Zn+{H2N(CH2)4CH(NH2)COONa}2SO4−] •H20," Chinese Science Bulletin, Sep. 1990, 35(18):1521-1525.
Gang Yi et al., Study on the inhibition activity of zinc amino acid chelate, Food Science, vol. 30, No. 17, pp. 84-87, Nov. 20, 2009.
Kumar, P., et al., Clinical Medicine, the 6th version (edition 1), Beijing University Medical Press, Aug. 31, 2008.
Sun Hui et al., Surgery and Dermatology and Venereology (first edition), pp. 274-275, Beijing Science and Technology Press, Jan. 31, 2009.
Dong Yinmao, Formulation design and production process for cosmetics, first edition, p. 372, China Textile & Apparel Press, Apr. 2007.

* cited by examiner

PERSONAL CLEANSING COMPOSITIONS CONTAINING ZINC AMINO ACID/TRIMETHYLGLYCINE HALIDE

CROSS REFERENCE TO RELATED APPLICATIONS

This application is a continuation in part of Application Nos. PCT/US2012/70489, filed on 19 Dec. 2012; PCT/US2012/70492, filed on 19 Dec. 2012; PCT/US2012/70498, filed on 19 Dec. 2012; PCT/US2012/70501, filed on 19 Dec. 2012; PCT/US2012/70505, filed on 19 Dec. 2012; PCT/US2012/70506, filed on 19 Dec. 2012; PCT/US2012/70513, filed on 19 Dec. 2012; PCT/US2012/70521, filed on 19 Dec. 2012; PCT/US2012/70525, filed on 19 Dec. 2012; PCT/US2012170534, filed on 19 Dec. 2012; PCT/US2012/70537, filed on 19 Dec. 2012; PCT/US2013/46268, filed on 18 Jun. 2013; PCT/US2013/50845, filed on 17 Jul. 2013; PCT/US2013/68852, filed on 7 Nov. 2013; PCT/US2013/68854, filed on 7 Nov. 2013; PCT/US2013/68859, filed on 7 Nov. 2013; PCT/US2013/68860, filed on 7 Nov. 2013, all of which are incorporated herein by reference.

BACKGROUND

It is extremely difficult to provide liquid personal wash compositions with sunscreen components or agents which sunscreen components may be readily deposited on the skin or other surface. One significant problem is that the sunscreen agents will generally be solubilized by the surfactant and, while they may be deposited during lathering, they will be removed by rinsing.

There is a need for additional cleansing compositions that provide delivery of sunscreen actives to the skin to provide enhanced sunscreen efficacy.

BRIEF SUMMARY

There is a personal cleansing composition which comprises
a) a skin cleansing effective amount of a surfactant, and
b) a zinc X halide present in an amount to provide at least 0.36 weight % of the composition of zinc,
wherein X is an amino acid or trimethylglycine.

Still further, there is a method for using the above identified composition for skin cleansing.

Provided is a personal cleansing composition, for example a shower gel, body wash, shampoo, conditioner, or soap bar, which delivers to the skin a zinc X halide, i.e., a complex of zinc ion, X residue, and halide ion, such as zinc lysine chloride ($ZnLys_2Cl_2$ or $ZnLysine_3Cl_2$). X refers to amino acid or trimethylglycine. Trimethylglycine as used throughout refers to N,N,N-trimethylglycine.

The complex solubilizes the zinc salt to allow for its delivery to skin or hair from a personal cleansing composition.

As the zinc X halide provides sunscreen properties, also provided is a method of reducing sun damage to the skin or protecting the skin from sunburn or sun damage, comprising washing the skin with the cleansing composition and water, prior to exposure to the sun.

Also, provided are methods of killing bacteria comprising contacting the bacteria with the composition.

Also, provided are method of reducing perspiration comprising washing skin with the composition.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

In accordance with the preferred embodiments, the composition is a liquid, typically an aqueous liquid, and may take the form of a shampoo, liquid soap or detergent, bubble bath, shower gel, body wash, or a conditioner.

The composition functions as a sunscreen and as a cleansing composition.

In one embodiment, provided is a composition comprising zinc X halide and/or zinc X halide precursor materials which form a zinc X halide in situ (for example zinc ion source plus an X hydrohalide, or zinc halide plus an X, or zinc ion source plus halogen acid plus X). The zinc ion source to produce the zinc X halide is a material that can release $Zn^{2+}$ in aqueous solution in the presence of an X, for example zinc oxide, tetrabasic zinc chloride, zinc chloride, zinc carbonate, zinc citrate, zinc nitrate, or zinc phosphate.

Provided is, in a first embodiment, a personal cleansing composition for application to the skin or hair which comprises a zinc X halide, one or more surfactants, (Composition 1), e.g., 1.1. Any of the foregoing compositions further comprising a cosmetically acceptable carrier.
1.2. Any of the foregoing compositions wherein the zinc X halide is formed from precursors wherein the precursors are a zinc ion source, an X source, and a halide source, wherein the halide source can be part of the zinc ion source, the X source, or a halogen acid.
1.3. The foregoing composition, wherein the zinc ion source is at least one of zinc oxide, zinc chloride, tetrabasic zinc chloride, zinc carbonate, zinc nitrate, zinc citrate, and zinc phosphate.
1.4. Compositions 1.2 or 1.3 wherein the X source is at least one of a basic amino acid, lysine, arginine, and glycine.
1.5. Any of the foregoing compositions wherein the zinc X halide is made by combining zinc oxide with an amino acid hydrohalide.
1.6. Any of the foregoing compositions wherein the zinc X halide is made by combining TBZC with an amino acid hydrohalide, an amino acid, or trimethylglycine, optionally the zinc X halide is made by combining TBZC with lysine, lysine hydrochloride, or trimethylglycine.
1.7. Any of the foregoing compositions wherein the zinc X halide has the formula $ZnX_3Hal_2$, wherein Zn is divalent zinc ion, X is amino acid or trimethylglycine residue, and Hal is halide ion.
1.8. Any of the foregoing compositions, wherein a total amount of zinc present in the composition is at least 0.37%, 0.36% to 10%, or 0.37 to 10%, or 0.36 to 5%, or 0.37 to 5%, or 0.4 to 5%, or 0.4 to 2%, or 0.4 to 1%, or 0.5 to 5%, or 0.5 to 4%, or 0.5 to 3%, or 0.5 to 2% by weight of the composition.
1.9. Any of the foregoing compositions, wherein the amino acid is lysine.
1.10. Any of the foregoing compositions, wherein the zinc X halide is present in an amount of 1.5 to 40% by weight of the composition, optionally at least 2, at least 3, or at least 4 up to 40% by weight of the composition, or, optionally, 1.5 up to 30%, up to 20%, up to 10%, up to 5%, up to 4%, up to 3%, up to 2%, or up to by weight of the composition.

1.11. Any of the foregoing compositions, wherein a molar ratio of zinc to X is 2:1 to 1:4, optionally 1:1 to 1:4, 1:2 to 1:4, 1:3 to 1:4, 2:1 to 1:3, 2:1 to 1:2, 2:1 to 1:1, or 1:3.

1.12. Any of the foregoing compositions, wherein the halide is selected from the group consisting of chloride, bromide, and iodide, preferably chloride.

1.13. Any of the foregoing compositions, wherein the zinc amino acid halide is zinc lysine chloride.

1.14. Any of the foregoing compositions in an anhydrous carrier.

1.15. Any of the foregoing compositions comprising a zinc amino acid halide formed from zinc oxide and an amino acid hydrohalide.

1.16. Any of the foregoing compositions, wherein the zinc amino acid halide is zinc lysine chloride ($ZnLysine_2Cl_2$ or $ZnLysine_3Cl_2$).

1.17. Any of the foregoing compositions wherein the surfactant is anionic, nonionic, amphoteric/zwitterionic, cationic or a mixture thereof.

1.18. Any of the foregoing compositions wherein the cosmetically acceptable carrier comprises water in an amount of 1 to 99%, or 50 to 95%, or 70 to 95%.

1.19. Any of the foregoing compositions, wherein the composition provides a SPF of at least 2, or at least 5, or at least 4, or at least 5 or at least 6, or at least 7, or at least 8, or at least 9, or at least 10, or at least 12, or at least 15, or at least 20, or at least 25, or at least 30, when applied to skin and/or hair in accordance with the method.

1.20. Any of the foregoing compositions, wherein the composition is a body wash, a shower gel, a shampoo, hair conditioner, or soap bar.

Also provided is a method of reducing sun damage to the skin or protecting the skin from sunburn or sun damage, comprising washing the skin with the cleansing composition, e.g., any of Composition 1, et seq. prior to exposure to the sun.

Also provided are methods of reducing perspiration comprising applying an antiperspirant effective amount of any of Composition 1, et seq. to the skin, methods of reducing body odor comprising applying a deodorant-effective amount of any of Composition 1, et seq. to the skin, and methods of killing bacteria comprising contacting the bacteria with an antibacterially effective amount of a zinc X halide composition, e.g., any of Composition 1, et seq.

Also provided is a method of making a composition comprising a zinc X halide, e.g., any of Composition 1, et seq.

Without intending to be bound by theory, it is believed that the formation of the zinc X halide proceeds via formation of the zinc halide then coordination of X residues around a central zinc. Using reaction of zinc oxide with lysine hydrochloride in water as an example, ZnO reacts with lysine HCl via dissociation of the hydrochloride to allow the reaction: $ZnO + HCl \rightarrow 7\ ZnCl_2 + H_2O$. One mole of $ZnCl_2$ will react with 3 moles of lysine to form a clear solution of Zn-lysine-chloride complex ($ZnLysine_2Cl_2$ or $ZnLysine_3Cl_2$), believed to have the structure depicted in Formula 1, wherein R denotes the X side chain:

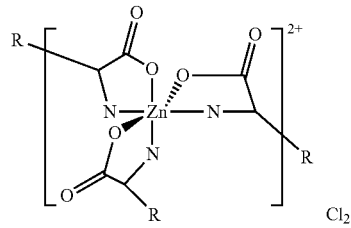

Formula 1

In this configuration, Zn is located in an octahedral center coordinated with two oxygen and two nitrogen atoms in the equatorial plane coming from two lysine's carboxylic acids and amine groups respectively. The zinc is also coordinated to the third lysine via its nitrogen and carboxylic oxygen, at the apical position of the metal geometry. This appears to be the dominant complex. Other complexes of zinc and lysine are possible, e.g., if there is insufficient halide, e.g., $ZnOLys_2$, having a pyramid geometry, with the equatorial plane that is same as the above compound (Zn is bound to two oxygen and two nitrogen atoms from different lysines), wherein the top of the pyramid is occupied by an O atom. More complex structures involving multiple zinc ions are also possible, based on the TBZC structure. The zinc can also have the zinc structure present in zinc stearate.

The interaction of zinc and X converts the insoluble ZnO or TBZC to a highly soluble complex at approximately neutral pH. In the skin, which contains charged molecules such as proteins and fatty acids, the complex will flocculate, forming a precipitate that deposits on the skin. To the extent the complex is disrupted in these conditions, releasing free zinc ion, the zinc ion can hydrolyze to form amorphous zinc hydroxide precipitate, further depositing on the skin, and moreover, the zinc ion can kill skin bacteria, thereby reducing odor. As the amount of water increases, the ZXH hydrolyzes to distribute a relatively insoluble zinc-containing precipitate. The precipitate typically contains one or more of zinc oxide, zinc cysteine, zinc hydroxide, or other zinc-containing compounds. This precipitate is unique in that it will allow deposition on the skin. Furthermore, this reaction is atypical since, in most cases, dilution will increase the solubility of an ionic complex.

It will be understood that other Xs can be used in place of lysine in the foregoing scheme. It will also be understood that, although the zinc, X and halide may be primarily in the form of precursor materials or in the form of a complex, there may be some degree of equilibrium, so that the proportion of material which is actually in complex compared to the proportion in precursor form may vary depending on the precise conditions of formulation, concentration of materials, pH, presence or absence of water, presence or absence of other charged molecules, and so forth.

The combination of the zinc, the X, and the halide forms a cationic complex-halide salt. The zinc X halide is a water soluble complex formed from the halide acid addition salt of zinc (e.g., zinc chloride) and an X, or from the halide acid addition salt of an X (e.g., lysine hydrochloride) and zinc ion source, e.g., zinc oxide or TBZC, and/or from combination of all three of a halogen acid, an X, and a zinc ion source.

The zinc ion source for combination with an amino acid hydrohalide or an X plus halogen acid may be any source that provides $Zn^{2+}$ ions efficiently, for example zinc oxide, zinc chloride, tetrabasic zinc chloride, zinc carbonate, zinc nitrate, zinc citrate, and zinc phosphate. Zinc oxide is a white powder, insoluble in water. Tetrabasic zinc chloride (TBZC) or zinc chloride hydroxide monohydrate is a zinc hydroxy compound with the formula $Zn_5(OH)_8Cl_2 \cdot H_2O$, also referred to as basic zinc chloride, zinc hydroxychloride, or zinc oxychloride. It is a colorless crystalline solid insoluble in water. Both of these materials are found to be soluble in water in the presence of an X and provide a source of zinc ions while restricting the available anions, as an excess of anions can interfere with the complex formation.

The amino acid source can be any amino acid. Examples of amino acids include, but are not limited to, the common natural amino acids, e.g.: lysine, arginine, histidine, glycine, serine, threonine, asparagine, glutamine, cysteine, selenocysteine, proline, alanine, valine, isoleucine, leucine, methionine, phenylalanine, tyrosine, tryptophan, aspartic acid, and glutamic acid.

In some embodiments, the amino acid is a basic amino acid. By "basic amino acid" is meant the naturally occurring basic amino acids, such as arginine, lysine, and histidine, as well as any basic amino acid having a carboxyl group and an amino group in the molecule, which is water-soluble and provides an aqueous solution with a pH of 7 or greater. Accordingly, basic amino acids include, but are not limited to, arginine, lysine, citrulline, ornithine, creatine, histidine, diaminobutanoic acid, diaminoproprionic acid, salts thereof or combinations thereof. In certain embodiments, the amino acid is lysine. In other embodiments, the amino acid is arginine. Neutral amino acids, such as glycine, and even acidic amino acids, such as aspartic acid, however, are also capable of forming salts with strong acids, such as halogen acids. In some embodiments the amino acid is a neutral or acidic amino acid, e.g., glycine.

The halide source can be part of the zinc source, such as zinc chloride or tetrabasic zinc chloride. The halide source can be part of the amino acid, such as an amino acid hydrohalide. Also, the halide source can be a halogen acid. The halide may be chlorine, bromine, or iodine, most typically chlorine. The acid addition salt of an amino acid and a halogen acid (e.g., HCl, HBr, or HI) is sometimes referred to herein as an amino acid hydrohalide. Thus one example of an amino acid hydrohalide is lysine hydrochloride.

The amount of zinc X halide in the compositions is a UVA radiation protecting amount. In one embodiment it is also a UVB radiation protecting about. Such an amount is sufficient to provide a SPF of at least 2 when applied to the skin and rinsing with water, e.g., washing with the composition for 30 seconds and rinsing with water for 30 seconds. In certain embodiments, the amount of zinc X halide in the composition provides at least 0.36% zinc by weight of the composition. In some embodiments the amount of zinc in the composition is at least 0.37%, in another embodiment 0.36 to 10%, in another embodiment 0.37 to 10%, in another embodiment 0.36 to 5%, in another embodiment 0.37 to 5%, in another embodiment 0.4 to 5%, in another embodiment 0.4 to 2%, in another embodiment 0.4 to 1%. To provide the desired levels of zinc, when zinc X halide powder is used the amount of the powder is at least 1.5%, in another embodiment 1.5 to 10%, in another embodiment 1.5 to 5%. When a zinc X halide solution is used, the amount of solution is at least 5%, in one embodiment 5 to 20%, in another embodiment 5 to 15%. In certain embodiments, precursors, e.g., zinc oxide and amino acid hydrohalide, are present in amounts such that when combined into the zinc X halide, the zinc X halide would be present in an amount of 1.5 to 10% by weight of the composition. In either of these embodiments, the amount of the zinc X halide can be varied for the desired purpose, such as an antibacterial agent or as a sunscreen. In other embodiments, the amount of the zinc X halide is at least 0.5, at least 1, at least 2, at least 3, or at least 4 up to 10% by weight of the composition. In other embodiments, the amount of the zinc X halide is less than 9, less than 8, less than 7, less than 6, less than 5, less than 4, less than 3, less than 2, or less than 1% by weight of the composition. In other embodiments, the amounts of zinc in the composition is 0.5 to 5%, 0.5 to 4%, 0.5 to 3%, or 0.5 to 2% by weight of the composition.

When the zinc X halide is formed from precursor materials, the precursor materials are preferably used in molar ratios approximately as required to produce the desired zinc X halide, although an excess of one material or another may be desirable in certain formulations, e.g., to balance pH against other formulation constituents, to provide additional antibacterial zinc, or to provide X buffer. Preferably, however, the amount of halide is limited, as constraining the level of halide somewhat encourages interaction between the zinc and the X. For example, in one embodiment to produce zinc lysine chloride ($ZnLysine_2Cl_2$ or $ZnLysine_3Cl_2$), the molar ratios of the elements in the precursor materials would include 1 molar equivalent $Zn^{2+}$:3 molar equivalents Lys:2 molar equivalents $Cl^-$.

In certain embodiments, a molar ratio of zinc to X is at least 2:1. In other embodiments, the molar ratio is at least 1:1, at least 1:2, at least 1:3, at least 1:4, 2:1 to 1:4, 1:1 to 1:4, 1:2 to 1:4, 1:3 to 1:4, 2:1 to 1:3, 2:1 to 1:2, 2:1 to 1:1, or 1:3. Above 1:4, it is expected that the zinc will be totally dissolved.

In certain embodiments, the zinc X halide can have a conductivity of greater than 8000, optionally greater than 9000, greater than 10,000, or greater than 12,000 µS/cm, preferably when the pH is at least 4.

In one embodiment, the composition provides cleansing activity, in such embodiment, there typically is a skin cleansing effective amount of a surfactant present in the composition.

Generally, at least 0.1 wt. % of the composition should be surfactant (a). Preferred minimums of at least 1, 3, 5, 7, 10, 20 and 30 wt. % surfactant(s) can be present in the composition. Maximum quantities of surfactant(s) depends upon the physical mixture of the composition being employed as well as the amount of additional components. Generally, no more than 95-97 wt. % surfactant(s) are present, specifically no more than 90 wt. % surfactant(s). Maximum quantities of 20, 30, 40, 50, 60, 70, 80, or 85 wt. % surfactant(s) can also be readily employed. In certain embodiments, the surfactant is present in an amount of 0.1 to 45, 1 to 15, 15 to 45, or 15-35 weight % of the composition depending on the type of composition. The cleaning composition is in liquid form and can be formulated to be body wash/shower gel, a shampoo, or a conditioner. The surfactant can be a surfactant or a combination of surfactants. Suitable surfactants include anionic, nonionic, cationic, amphoteric, or zwitterionic surfactants. The term surfactant includes salts of fatty acids, which are typically referred to as soaps.

Suitable anionic surfactants include, but are not limited to, those surface-active or detergent compounds that contain an organic hydrophobic group containing generally 8 to 26 carbon atoms or generally 10 to 18 carbon atoms in their molecular structure and at least one water-solubilizing group selected from sulfonate, sulfate, and carboxylate so as to form a water-soluble detergent. Usually, the hydrophobic group will comprise a $C_8$-$C_{22}$ alkyl, or acyl group. Such surfactants are employed in the form of water-soluble salts and the salt-forming cation usually is selected from sodium, potassium, ammonium, magnesium and mono-, di- or tri- $C_2$-$C_3$ alkanolammonium, with the sodium, magnesium and ammonium cations again being the usual ones chosen.

Suitable anionic surfactants include, but are not limited to, the sodium, potassium, ammonium, and ethanolammonium salts of linear $C_8$-$C_{16}$ alkyl benzene sulfonates, alkyl ether carboxylates, $C_{10}$-$C_{20}$ paraffin sulfonates, $C_8$-$C_{25}$ alpha olefin sulfonates, $C_2$-$C_{18}$ alkyl sulfates, $C_8$-$C_{18}$ alkyl ether sulfates and mixtures thereof.

Other suitable anionic surfactants include paraffin sulfonates, which may be monosulfonates or di-sulfonates and usually are mixtures thereof, obtained by sulfonating paraffins of 10 to 20 carbon atoms. Commonly used paraffin sulfonates are those of $C_{12}$-$C_{18}$ carbon atoms chains, and more commonly they are of $C_{14}$-$C_{17}$ chains. Paraffin sulfonates that have the sulfonate group(s) distributed along the paraffin chain are described in U.S. Pat. Nos. 2,503,280; 2,507,088; 3,260,744; and 3,372,188; and also in German Patent 735,096. Such compounds may be made to specifications and desirably the content of paraffin sulfonates outside the $C_{14}$-$C_{17}$ range will be minor and will be minimized, as will be any contents of di- or poly-sulfonates. Examples of paraffin sulfonates include, but are not limited to HOSTAPUR™ SAS30, SAS 60, SAS 93 secondary alkane sulfonates from Clariant, and BIO-TERGE™ surfactants from Stepan, and CAS No. 68037-49-0.

Examples of suitable other sulfonated anionic surfactants include higher alkyl mononuclear aromatic sulfonates, such as the higher alkylbenzene sulfonates containing 9 to 18 or 9 to 16 carbon atoms in the higher alkyl group in a straight or branched chain, or $C_8$-$C_{15}$ alkyl toluene sulfonates. In one embodiment, the alkylbenzene sulfonate is a linear alkylbenzene sulfonate having a higher content of 3-phenyl (or higher) isomers and a correspondingly lower content (well below 50%) of 2-phenyl (or lower) isomers, such as those sulfonates wherein the benzene ring is attached mostly at the 3 or higher (for example 4, 5, 6 or 7) position of the alkyl group and the content of the isomers in which the benzene ring is attached in the 2 or 1 position is correspondingly low. Materials that can be used are found in U.S. Pat. No. 3,320,174, especially those in which the alkyls are of 10 to 13 carbon atoms.

Other suitable anionic surfactants include the olefin sulfonates, including long-chain alkene sulfonates, long-chain hydroxyalkane sulfonates or mixtures of alkene sulfonates and hydroxyalkane sulfonates. These olefin sulfonate detergents may be prepared in a known manner by the reaction of sulfur trioxide ($SO_3$) with long-chain olefins containing 8 to 25, or 12 to 21 carbon atoms and having the formula $RCH=CHR_1$ where R is a higher alkyl group of 6 to 23 carbons and RI is an alkyl group of 1 to 17 carbons or hydrogen to form a mixture of sultones and alkene sulfonic acids which is then treated to convert the sultones to sulfonates. In one embodiment, olefin sulfonates contain from 14 to 16 carbon atoms in the R alkyl group and are obtained by sulfonating an a-olefin.

Examples of satisfactory anionic sulfate surfactants include alkyl sulfate salts and ether sulfate salts. Suitable anionic ether sulfate has the formula $R(OC_2H_4)_n OSO_3M$ wherein n is 1 to 12, or 1 to 5, and R is an alkyl, alkylaryl, acyl, or alkenyl group having 8 to 18 carbon atoms, for example, an alkyl group of $C_{12}$-$C_{14}$ or $C_{12}$-$C_{16}$, and M is a solubilizing cation selected from sodium, potassium, ammonium, magnesium and mono-, di- and triethanol ammonium ions. Exemplary alkyl ether sulfates contain 12 to 15 carbon atoms in the alkyl groups thereof, e.g., sodium myristyl (3 EO) sulfate. Suitable alkylaryl ether sulfates include $C_8$-$C_{18}$ alkylphenyl ether sulfates containing from 2 to 6 moles of ethylene oxide in the molecule.

Other suitable anionic detergents include the $C_9$-$C_{15}$ alkyl ether polyethenoxyl carboxylates. Suitable alkyl ether polyethoxyl carboxylates may be prepared by condensing ethylene oxide with appropriate alkanol and reacting this reaction product with chloracetic acid to make the ether carboxylic acids as shown in U.S. Pat. No. 3,741,911 or with succinic anhydride or phtalic anhydride.

Suitable nonionic surfactants utilized include the primary aliphatic alcohol ethoxylates, secondary aliphatic alcohol ethoxylates, alkylphenol ethoxylates and ethylene-oxide-propylene oxide condensates on primary alkanols, such a PLURAFAC™ surfactants (BASF) and condensates of ethylene oxide with sorbitan fatty acid esters such as the TWEEN™ surfactants (ICI). The nonionic synthetic organic detergents generally are the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a water-soluble nonionic detergent. Further, the length of the polyethenoxy chain can be adjusted to achieve the desired balance between the hydrophobic and hydrophilic elements.

The nonionic surfactant class includes the condensation products of a higher alcohol (e.g., an alkanol containing 8 to 18 carbon atoms in a straight or branched chain configuration) condensed with 5 to 30 moles of ethylene oxide, for example, lauryl or myristyl alcohol condensed with 16 moles of ethylene oxide (EO), tridecanol condensed with 6 to moles of EO, myristyl alcohol condensed with 10 moles of EO per mole of myristyl alcohol, the condensation product of EO with a cut of coconut fatty alcohol containing a mixture of fatty alcohols with alkyl chains varying from 10 to 14 carbon atoms in length and wherein the condensate contains either 6 moles of EO per mole of total alcohol or 9 moles of EO per mole of alcohol and tallow alcohol ethoxylates containing 6 EO to 11 EO per mole of alcohol.

Desirably suitable nonionic surfactants include the NEODOL™ ethoxylates (Shell Co.), which are higher aliphatic, primary alcohol containing 9-15 carbon atoms, such as $C_9$-$C_{11}$ alkanol condensed with 2 to 10 moles of ethylene oxide (NEODOL™ 91-2.5 OR -5 OR -6 OR -8), $C_{12}$-$C_{13}$ alkanol condensed with 6 to 7 moles ethylene oxide (NEODOL™ 23-6.5), $C_{12}$-$C_{15}$ alkanol condensed with 12 moles ethylene oxide (NEODOL™ 25-12), $C_{14}$-$C_{15}$ alkanol condensed with 13 moles ethylene oxide (NEODOL™ 45-13), and the like.

Additional satisfactory water soluble alcohol ethylene oxide condensates are the condensation products of a secondary aliphatic alcohol containing 8 to 18 carbon atoms in a straight or branched chain configuration condensed with 5 to 30 moles of ethylene oxide. Examples of commercially available nonionic detergents of the foregoing type are $C_{11}$-$C_{15}$ secondary alkanol condensed with either 9 EO (TERGITOL™ 15-S-9) or 12 EO (TERGITOL™ 15-S-12) marketed by Union Carbide.

Other suitable nonionic surfactants include the polyethylene oxide condensates of one mole of alkyl phenol containing from 8 to 18 carbon atoms in a straight- or branched chain alkyl group with 5 to 30 moles of ethylene oxide. Specific examples of alkyl phenol ethoxylates include, but are not limited to, nonyl phenol condensed with 9.5 moles of EO per mole of nonyl phenol, dinonyl phenol condensed with 12 moles of EO per mole of phenol, dinonyl phenol condensed with 15 moles of EO per mole of phenol and di-isoctylphenol condensed with 15 moles of EO per mole of phenol. Commercially available nonionic surfactants of this type include IGEPAL™ CO-630 (nonyl phenol ethoxylate) marketed by GAF Corporation.

Also among the satisfactory nonionic surfactants are the water-soluble condensation products of a $C_8$-$C_{20}$ alkanol with a heteric mixture of ethylene oxide and propylene oxide wherein the weight ratio of ethylene oxide to propylene oxide is from 2.5:1 to 4:1, or 2.8:1 to 3.3:1, with the total of the ethylene oxide and propylene oxide (including the terminal ethanol or propanol group) being from 60-85%, or 70-80%, by weight. Such detergents are commercially available from BASF and a particularly preferred surfactant is a $C_{10}$-$C_{16}$ alkanol condensate with ethylene oxide and propylene oxide, the weight ratio of ethylene oxide to propylene oxide being 3:1 and the total alkoxy content being 75% by weight.

Condensates of 2 to 30 moles of ethylene oxide with sorbitan mono- and tri-$C_{10}$-$C_{20}$ alkanoic acid esters having a HLB of 8 to 15 also may be employed as the nonionic detergent ingredient in the described composition. These surfactants are well known and are available from Imperial Chemical Industries under the TWEEN™ trade name. Suitable surfactants include, but are not limited to, polyoxyethylene (4) sorbitan monolaurate, polyoxyethylene (4) sorbitan monostearate, polyoxyethylene (20) sorbitan trioleate and polyoxyethylene (20) sorbitan tristearate.

Other suitable water-soluble nonionic surfactants are marketed under the trade name PLURONIC™. The compounds are formed by condensing ethylene oxide with a hydrophobic base formed by the condensation of propylene oxide with propylene glycol. The molecular weight of the hydrophobic portion of the molecule is of the order of 950 to 4000 or 200 to 2,500. The addition of polyoxyethylene radicals to the hydrophobic portion tends to increase the solubility of the molecule as a whole so as to make the surfactant water-soluble. The molecular weight of the block polymers varies from 1,000 to 15,000 and the polyethylene oxide content may comprise 20% to 80% by weight. In one embodiment, these surfactants will be in liquid form and satisfactory surfactants are available as grades L 62 and L 64.

Alkyl polysaccharides surfactants, which can be used in the instant composition, have a hydrophobic group containing from 8 to 20 carbon atoms, or from 10 to 16 carbon atoms, or from 12 to 14 carbon atoms, and polysaccharide hydrophilic group containing from 1.5 to 10, or from 1.5 to 4, or from 1.6 to 2.7 saccharide units (e.g., galactoside, glucoside, fructoside, glucosyl, fructosyl; and/or galactosyl units). Mixtures of saccharide moieties may be used in the alkyl polysaccharide surfactants. The number x indicates the number of saccharide units in a particular alkyl polysaccharide surfactant. For a particular alkyl polysaccharide molecule x can only assume integral values. In any physical sample of alkyl polysaccharide surfactants there will be in general molecules having different x values. The physical sample can be characterized by the average value of x and this average value can assume non-integral values. In this specification the values of x are to be understood to be average values. The hydrophobic group (R) can be attached at the 2-, 3-, or 4-positions rather than at the 1-position, (thus giving e.g. a glucosyl or galactosyl as opposed to a glucoside or galactoside). However, attachment through the 1-position, i.e., glucosides, galactoside, fructosides, etc., is preferred. In one embodiment, the additional saccharide units are predominately attached to the previous saccharide unit's 2-position. Attachment through the 3-, 4-, and 6-positions can also occur. Optionally and less desirably there can be a polyalkoxide chain joining the hydrophobic moiety (R) and the polysaccharide chain. The preferred alkoxide moiety is ethoxide.

Typical hydrophobic groups include alkyl groups, either saturated or unsaturated, branched or unbranched containing from 8 to 20, or from 10 to 18 carbon atoms. In one embodiment, the alkyl group is a straight chain saturated alkyl group. The alkyl group can contain up to 3 hydroxy groups and/or the polyalkoxide chain can contain up to 30, or less than 10, alkoxide moieties.

Suitable alkyl polysaccharides include, but are not limited to, decyl, dodecyl, tetradecyl, pentadecyl, hexadecyl, and octadecyl, di-, tri-, tetra-, penta-, and hexaglucosides, galactosides, lactosides, fructosides, fructosyls, lactosyls, glucosyls and/or galactosyls and mixtures thereof.

The alkyl monosaccharides are relatively less soluble in water than the higher alkyl polysaccharides. When used in a mixture with alkyl polysaccharides, the alkyl monosaccharides are solubilized to some extent. Suitable mixtures include coconut alkyl, di-, tri-, tetra-, and pentaglucosides and tallow alkyl tetra-, penta-, and hexaglucosides.

"Alkyl polysaccharide surfactant" is intended to represent both the glucose and galactose derived surfactants and the alkyl polysaccharide surfactants. Throughout this specification, "alkyl polyglucoside" is used to include alkyl polyglycosides because the stereochemistry of the saccharide moiety is changed during the preparation reaction.

Suitable alkyl polyglucosides include APG 625 glycoside manufactured by the Henkel Corporation of Ambler, Pa. APG 625 is a nonionic alkyl polyglycoside characterized by the formula:

$$C_nH_{2n+1}O(C_6H_{10}O_5)_xH$$

wherein n=10 (2%); n=122 (65%); n=14 (21-28%); n=16 (4-8%) and n=18 (0.5%) and x (degree of polymerization)= 1.6. APG 625 has: a pH of 6 to 10 (10% of APG 625 in distilled water); a specific gravity at 25° C. of 1.1 g/ml; a density at 25° C. of 9.1 lbs/gallon; a calculated HLB of 12.1 and a Brookfield viscosity at 35° C. 21 spindle. 5-10 RPM of 3,000 to 7,000 cps.

Suitable zwitterionic surfactants include betaines and sultaines. Typical alkyldimethyl betaines include, but are not limited to, decyl dimethyl betaine or 2-(N-decyl-N, N-dimethylammonia)acetate, coco dimethyl betaine or 2-(N-coco N, N-dimethylammonia)acetate, myristyl dimethyl betaine, palmityl dimethyl betaine, lauryl dimethyl betaine, cetyl dimethyl betaine, stearyl dimethyl betaine, etc. The amidobetaines similarly include, but are not limited to, cocoamidoethylbetaine, cocoamidopropyl betaine and the like. The amidosulfobetaines include, but are not limited to, cocoamidoethylsulfobetaine, cocoamidopropyl sulfobetaine and the like. In one embodiment, the betaine is coco ($C_8$-$C_{18}$) amidopropyl dimethyl betaine. Three examples of betaine surfactants that can be used are EMPIGEN™ BS/CA from Albright and Wilson, REWOTERIC™ AMB 13 and Goldschmidt Betaine L7.

Other suitable zwitterionic surfactants include amine oxides.

The above ethylene oxide condensates, amides, and amine oxides are more fully described in U.S. Pat. No. 4,316,824. A preferred amine oxide is cocoamidopropyl-dimethylamine oxide.

One desirable surfactant for the cleaning composition is an alkyl benzene sulfonate surfactant. Another desirable surfactant is a surfactant system of a combination of an alkyl ether sulfonate, and a zwitterionic surfactant. Yet another desirable is a surfactant system of a combination of an alkyl benzene sulfonate, an alkyl ether sulfonate, and a zwitterionic surfactant. It may be desirable to include the cationic surfactant(s) in an amount of up to 25% by weight, or up to 10% by weight, or up to 3% by weight, of the total composition. It may be desirable to include the nonionic surfactant(s) in an amount of up to 20% by weight, or up to 10% by weight, or up to 5% by weight of the total composition. In an embodiment it may be desirable to include the alkyl benzene sulfonate salt surfactant(s) in an amount of 1% to 40% by weight, or 3% by weight to 30% by weight, or 5% to 20% by weight of the total composition, with attention to the relative ratio various salts (of applicable), e.g., sodium to magnesium salts, as described above. In an embodiment it may be desirable to include the alkyl ether sulfate surfactant(s) in an amount of 5% to 40% by weight, or 10% to 25% by weight, or 7% to 19% by weight. In an embodiment it may be desirable to include the amine oxide surfactant(s) in an amount of up to 25% by weight, or 5% to 20% by weight, or 2% to 10% by weight. In an embodiment it may be desirable to include the amphoteric surfactant(s) in an amount of up to 30% by weight, or up to 20% by weight, or up to 10% by weight.

The carrier represents all other materials in the composition other than the zinc X halide and surfactant. The amount of carrier is then the amount to reach 100% by adding to the weight of the zinc X halide plus surfactant.

The carrier typically includes water. The water typically is pure and deionized. The amount of water is 1 to 99%, or 50 to 95% or 70 to 95% by weight of the composition. In alternate embodiments, the composition is anhydrous. By anhydrous, there is less than 5% by weight water, optionally less than 4, less than 3, less than 2, less than 1, less than 0.5, less than 0.1 down to 0% by weight water.

The compositions may comprise further ingredients such as ingredients for skin lightening; tanning prevention; treatment of hyperpigmentation; preventing or reducing acne, wrinkles, lines, atrophy and/or inflammation; chelators and/or sequestrants; anti-cellulites and slimming (e.g. phytanic acid), firming, moisturizing and energizing, self tanning, soothing, as well as agents to improve elasticity and skin barrier and/or further UV-filter substances and carriers and/or excipients or diluents conventionally used in topical compositions.

The compositions can also contain usual cosmetic or cleaning adjuvants and additives, such as water-soluble alcohols; glycols; glycerides; medium to long chain organic acids, alcohols and esters; additional amino acids; structurants; emollients; preservatives/antioxidants; fatty substances/oils; organic solvents, silicones; thickeners; softeners; emulsifiers; other active sunscreen agents; moisturizers; aesthetic components such as fragrances; fillers; sequestering agents; anionic, cationic, nonionic or amphoteric polymers; propellants; acidifying or basifying agents; dyes; colorings/colorants; abrasives; absorbents; essential oils; skin sensates; astringents; pigments or nanopigments; e.g. those suited for providing a photoprotective effect by physically blocking out ultraviolet radiation; plants, herbs or parts or extracts thereof, e.g., seaweed; or any other ingredients usually formulated into cosmetic or cleaning compositions. Such ingredients commonly used in the skin care industry, which are suitable for use in the compositions, are e.g. described in the CTFA Cosmetic Ingredient Handbook, Second Edition (1992) without being limited thereto. The necessary amounts of the cosmetic and dermatological adjuvants and additives can be based on the desired product and be easily be chosen by a skilled person in this field.

For example, the composition may include one or more of fragrance compounds. The fragrance compound can be a fragrance precursor material, which upon a pH change, can release a fragrance. Also, the fragrance can be encapsulated. A wide variety of odiferous chemical compounds can be included in the film composition. Fragrance compounds include compounds used as perfumes and fragrances such as aldehydes, e.g., C6-C14 alipatic aldehydes and C6-C14 acyclic terpene aldehydes, ketones, alcohols, and esters. Suitable fragrance compounds include citral; neral; iso-citral; dihydro citral; citronellal; octanal; nonanal; decanal; undecanal; dodecanal; tridecanal; 2-methyl decanal; methyl nonyl acetaldehyde; 2-nonen-1-al; decanal; undecenal; undecylenic aldehyde; 2,6 dimethyl octanal; 2,6,10-trimethyl-9-undece-1-nal; trimethyl undecanal; dodecenal; melonal; 2-methyl octanal; 3,5,5, trimethyl hexanal and mixtures thereof. Fragrances may also include pro-fragrances such as acetal pro-fragrances, ketal pro-fragrances, ester pro-fragrances (e.g., digeranyl succinate), hydrolyzable inorganic-organic profragrances, and mixtures thereof. These pro-fragrances may release the perfume material as a result of simple hydrolysis. The composition may include 0.01% to 5% of a fragrance compound based on the total solid weight of the composition.

Other specific examples of optional ingredients include organic solvents, such as ethanol; thickeners, such as carboxymethylcellulose, magnesium aluminum silicate, hydroxyethylcellulose, methylcellulose, carbopols, glucamides, or Antil(R) from Rhone Poulenc; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, TiO2, EGMS (ethylene glycol monostearate) or Lytron 621 (Styrene/Acrylate copolymer); all of which are useful in enhancing the appearance or cosmetic properties of the product.

Examples of an additional antimicrobial is 2-hydroxy-4, 2'4'trichlorodiphenylether (DP300), lactic acid, quaternary ammonium compounds such as triclosan, and the like; examples of preservatives include dimethyloldimethylhydantoin (Glydant XL 1000), parabens, sorbic acid and the like.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) and Vitamin A, C & E or their derivatives may be used advantageously in amounts of 0.01% or higher if appropriate.

Polyethylene glycols which may be used include:
Polyox WSR-205 PEG 14M,
Polyox WSR-N-60K PEG 45M, or
Polyox WSR-N-750 PEG 7M.

Thickeners which may be used include Amerchol Polymer HM 1500 (Nonoxynyl Hydroethyl Cellulose); Glucam DOE 120 (PEG 120 Methyl Glucose Dioleate); Rewoderm (R) (PEG modified glyceryl cocoate, palmate or tallowate) from Rewo Chemicals; Antil(R) 141 (from Goldschmidt).

Another ingredient which may be included are exfoliants such as polyoxyethylene beads, walnut sheets and apricot seeds.

The amounts of optional carrier ingredients can, based on the desired product, easily be determined by the skilled person.

The optional carrier ingredients useful herein can in some instances provide more than one benefit or operate via more than one mode of action.

The compositions in general have a pH in the range of 3 to 10, in one embodiment a pH in the range of 4 to 8 and in another embodiment a pH in the range of 4 to 7. The pH can easily be adjusted as desired with suitable acids such as e.g. citric acid or bases such as NaOH according to standard methods in the art.

The compositions can be used in a method to reduce sweating by applying the composition to skin. In certain embodiments, the application is to axilla. Also, the compositions can be used to kill bacteria by contacting bacteria with the composition. For example, in one embodiment, the combination of the amino acid or amino acid hydrohalide with the zinc oxide increases the availability of zinc ions, which can then kill bacteria and reduce sweat.

Provided is (i) a method for controlling perspiration comprising applying to skin an antiperspirant effective amount of a formulation of any embodiment embraced or specifically described herein, e.g., any of Compositions 1 et seq.; and (ii) a method for controlling odor from perspiration comprises applying to skin a deodorant effective amount of a formulation of any embodiment embraced or specifically described herein, e.g., any of Compositions 1 et seq.

Further provided is a method of reducing sun damage to the skin or protecting the skin from sunburn or sun damage, comprising washing the skin with the liquid cleansing composition, e.g., any of Composition 1, et seq., and water, prior to exposure to the sun. Also applies to any part of the body that may be exposed to the sun, e.g. hair or nails. This method takes advantage of the unique aspect of the zinc X halide, i.e, depositing a zinc precipitate on the skin, nails or hair after dilution with water that occurs during typical washing. The deposited zinc acts as a sunscreen, absorbing UVA and/or UVB rays. Thus the method is a "rinse off" method, depositing sufficient zinc on the body after washing with the composition to provide an SPF of at least 2. The skin, hair or nails is typically washed with the composition for 5 seconds to 2 minutes, in one embodiment 5 to 30 seconds.

In one embodiment, the composition has the ability to protect skin from UVA and/or UVB rays while avoiding significant skin irritation. The composition should further be used in an amount sufficient to provide sun protective factor (SPF) of at least 2, preferably at least 2.5, more preferably at least 3.0. In one embodiment the composition has a SPF value ranging from 2 to 45. SPF is a commonly used measure of photo protection of a sunscreen against erythema. This number is derived from another parameter, the minimal erythemal dose (MED). MED is defined as the "least exposure dose at a specified wavelength that will elicit a delayed erythema response." The MED indicates the amount of energy irradiating the skin and the responsiveness of the skin to the radiation. The SPF of a particular photo protector is obtained by dividing the MED of protected skin by the MED of unprotected skin. The higher the SPF, the more effective the agent in preventing sunburn. The SPF value tells how many times longer a person can stay in the sun person will experience 1 MED. For example, utilizing a sunscreen with an SPF of 6 will allow an individual to stay in the sun six times longer before receiving 1 MED. As the SPF value of a sunscreen increases, the less chance exists for development of tanning of the skin. SPF is determined according to the procedures listed in 21 CFR 352 et seq. (in particular, 21 CFR 352.72 and 352.73).

Unless stated otherwise, all percentages of composition components given in this specification are by weight based on a total composition or formulation weight of 100%.

Unless otherwise specifically identified, the ingredients for use in the compositions and formulations are preferably cosmetically acceptable ingredients. By "cosmetically acceptable" is meant suitable for use in a formulation for topical application to human skin. A cosmetically acceptable excipient, for example, is an excipient which is suitable for external application in the amounts and concentrations contemplated in the formulations, and includes for example excipients which are "Generally Recognized as Safe" (GRAS) by the United States Food and Drug Administration.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the composition extends to the product of the combination of the listed ingredients.

EXAMPLE 1

Zinc Lysine Chloride Preparation 18.2650 g (0.1 mole) of L-LysineHCl is dissolved in 100 ml of Deionized water at room temperature under stirring. After all L-LysineHCl dissolves, 4.1097 g (0.0505 mole) of ZnO is slowly added into the solution under stirring. The suspension is continued mixing at room temperature for at least 30 minutes to 24 hours. Then, the suspension solution is centrifuged at 7000 rpm for 20 minutes and filtered through filter membrane with 0.45 µm pore size to remove unreacted ZnO. The clear supernatant is recovered as stock solution. A stock solution as prepared herein has typical zinc loading of 2.0% to 3.0% by weight and pH ranges from 6.8 to 7.2. Zinc loading can be readily determined using Inductively Coupled Plasma Atomic Emission Spectroscopy(ICP-AES) after acidification with a strong acid, such as nitric acid, or using any other suitable analytical method. Compositions involving other amino acids can be similarly prepared. In addition, an acid (such as HCl) can be added during the reaction or to the filtered stock solution to reduce pH and a base (such as NaOH, or KOH) can be added similarly to enhance pH. Powder is prepared by spray drying. The zinc lysine chloride complex described in this Example is sometimes referred to herein as "ZLC".

EXAMPLE 2

TBZC-Lys Preparation 14.6190 g (0.1 mole) of L-Lysine is dissolved in 100 ml of Deionized water at room temperature under stirring. After all L-Lysine dissolves, 5.5740 g (0.0101 mole) of TBZC is slowly added into the solution under stirring. The suspension is continued mixing at room temperature for at least 30 minutes to 24 hours. Then, the suspension solution is centrifuged at 7000 rpm for 20 minutes and filtered through filter membrane with 0.45 µm pore size to remove unreacted TBZC. The yellow clear supernatant is recovered as stock solution. A stock solution as prepared herein has typical zinc loading of 1.5% to 2.5% by weight and pH ranges from 10.5 to 11. Zinc loading can be readily determined using Inductively Coupled Plasma Atomic Emission Spectroscopy(ICP-AES) after acidification with a strong acid, such as nitric acid, or using any other suitable analytical method. Compositions involving other amino acids can be similarly prepared. In addition, an acid (such as HCl) can be added during the reaction or to the filtered stock solution to reduce pH and a base (such as NaOH, or KOH) can be added similarly to enhance pH. The powder is prepared by spray drying.

EXAMPLE 3

Preparation of Shower Gels with Zinc Lysine Chloride

Materials:
4.73% ZLC solution (Example 1)
15.7% ZLC powder (Example 1)
Shower Gel Using the Following Formulation in Table 1:

TABLE 1

| Material | Amount (weight %) |
| --- | --- |
| Demineralized water and minors (preservatives color, fragrance, pH agent) | Q.S. |
| Sodium laureth sulfate | 5.3 |
| Cocamidopropyl betaine | 3.5 |
| PPG-2 hydroxyethyl cocamide | 1.4 |
| Glycerin | 1 |
| Glycol distearate | 0.7 |
| Cocamide MEA | 0.5 |
| Polyquaternium-7 | 0.2 |
| trichlorocarbanilide | 0.2 |
| Ethoxylated fatty alcohol | 0.1 |
| Poloxamer 124 (EO-PO block copolymer) | 0.02 |

Six samples of ZLC powder in Shower Gel and six samples of ZLC solution in Shower Gel were created using the following procedure:

Six different mixtures containing various quantities of ZLC powder (15.7% Zn in ZLC powder) were made using the following formulations:

P1) 0.75% ZLC: 0.15 g ZLC powder was added to 19.85 g Shower Gel

The percent zinc in the mixture is 0.18%

P2) 1.5% ZLC: 0.3 g ZLC powder was added to 19.7 g Shower Gel

The percent zinc in the mixture is 0.36%

P3) 3% ZLC: 0.6 g ZLC powder was added to 19.4 g Shower Gel

The percent zinc in the mixture is 0.73%

P4) 5% ZLC: 1 g ZLC powder was added to 19 g Shower Gel

The percent zinc in the mixture is 1.23%

P5) 7% ZLC: 1.4 g ZLC powder was added to 18.6 g Shower Gel

The percent zinc in the mixture is 1.75%

P6) 10% ZLC: 2 g ZLC powder was added to 18 g Shower Gel

The percent zinc in the mixture is 2.56%

The mixtures were then stirred by hand with the use of a stirring rod for at least 5 minutes. They were then placed in a 50° C. oven for 5 days.

Six different mixtures containing various quantities of ZLC solution (4.73% Zn in ZLC solution) were made using the following formulations:

S1) 2.5% ZLC: 0.5 g ZLC solution was added to 19.5 g Shower Gel

The percent zinc in the mixture is 0.18%

S2) 5% ZLC: 1 g ZLC solution was added to 19 g Shower Gel

The percent zinc in the mixture is 0.37%

S3) 10% ZLC: 2 g ZLC solution was added to 18 g Shower Gel

The percent zinc in the mixture is 0.78%

S4) 15% ZLC: 3 g ZLC solution was added to 17 g Shower Gel

The percent zinc in the mixture is 1.24%

S5) 20% ZLC: 4 g ZLC solution was added to 16 g Shower Gel

The percent zinc in the mixture is 1.75%

S6) 25% ZLC: 5 g ZLC solution was added to 15 g Shower Gel

The percent zinc in the mixture is 2.32%

The mixtures were then stirred by hand with the use of a stirring rod for at least 5 minutes. They were then placed in a 50° C. oven for 5 days.

A sample of just Shower Gel was also placed in the 50° C. oven and aged for 5 days.

After aging, the viscosity of 0.7 cc of each sample was measured at 25° C. using an ARG2 instrument. A 40 mm 2 degree steal cone 9991511 was used to measure the viscosity using a shear only flow procedure.

Additionally, three more shower gel samples were later made ready for comparison. These samples contained 0% ZLC, 2% ZLC and 3% ZLC using the following formulation P0) 0% ZLC: 0 g ZLC powder was added to 20 g Shower Gel The percent zinc in the mixture is 0%

P7) 2% ZLC: 0.4 g ZLC powder was added to 19.6 g Shower Gel

The percent zinc in the mixture is 0.49%

P3) 3% ZLC: 0.6 g ZLC powder was added to 19.4 g Shower Gel

The percent zinc in the mixture is 0.73%

EXAMPLE 5

Deposit of Zinc on Human Skin after Washing with Zinc Lysine Halide Shower Gels Zinc deposit was measured using a hand washing procedure with the use of a Zincon indicator. A glove was cut so that only the finger tip of a single finger was exposed. The finger was cleaned thoroughly and dried. The hand was slightly rinsed with water and 0.5 cc of P1 was placed on the finger. The finger was scrubbed for 30 seconds. The finger was then rinsed for 30 seconds. Following drying, the finger was immediately sprayed with Zincon indicator. The turning of the orange-red color of Zincon indicator to a purple color indicated the presence of zinc. This procedure was repeated using a different finger each time for P2, P7, P3, S1, S2, S3 and original shower gel to determine the minimum amount of ZLC that would still leave a zinc deposit after washing.

P2 containing 0.36% zinc and S2 containing 0.37% zinc, both showing significant zinc deposit, along with P0, were diluted 2 fold, 4 fold, 8 fold, 16 fold and 32 fold to examine the formation of precipitate upon dilution using a Turbiscan at 37.5° C. The dilutions are shown in Table 2.

TABLE 2

|  | 2x | 4x | 8x | 16x | 32x |
|---|---|---|---|---|---|
| Mass Shower Gel Mixture (g) | 6 | 9 | 1.5 | 0.75 | 0.375 |
| Mass DI water (g) | 6 | 9 | 10.5 | 11.25 | 11.625 |

Results

A finger washed with regular Shower Gel only, had an orange-red color of Zincon indicator which shows no Zn deposition on skin. A finger washed with 2.5% ZLC solution in Shower Gel containing 0.18% Zn, had a mostly orange-red color of Zincon indicator which shows very little Zn deposition on skin. A finger washed with 5% ZLC solution in Shower Gel containing 0.37% Zn, has a purple color of Zincon indicator which shows significant Zn deposition on skin. A finger washed with 10% ZLC solution in Shower Gel containing 0.78% Zn, has a deep purple-blue color of Zincon indicator which shows significant Zn deposition on skin.

A finger washed with regular Shower Gel, has an orange-red color of Zincon indicator which shows no Zn deposition on skin. A finger washed with 0.75% ZLC powder in Shower Gel containing 0.18% Zn, has little purple color of Zincon indicator which shows a little Zn deposition on skin. A finger washed with 1.5% ZLC powder in Shower Gel containing 0.36% Zn, has a purple color of Zincon indicator which shows Zn deposition on skin. A finger washed with 3% ZLC powder in Shower Gel containing 0.73% Zn, has a deep purple-blue color of Zincon indicator which shows significant Zn deposition on skin.

A finger washed with Sample P0 containing 0% ZLC in Shower Gel, has an orange-red color of Zincon indicator which shows no Zn deposition on skin. A finger washed with P7 containing 2% ZLC in Shower Gel, has a purple color of Zincon Indicator which shows zinc deposition. A finger washed with P3 containing 3% ZLC in Shower Gel, has a purple color of Zincon indicator which shows significant Zn deposition on skin Turbidity Studies For solutions containing regular shower gel, all of the dilutions slowly increase in percent transmission during a 20 minute measurement period. All of the solutions are turbid from the very beginning. The 4 fold dilution initially has close to 0% transmission. The 2 fold and 16 fold dilutions have similar initial percent transmissions at around 1%. The 32 fold dilution has an instant percent transmission of 5.7% and the 8 fold dilution has an initial percent transmission of 6.5. The 2 fold dilution has the greatest increase in percent transmission during the measurement period, possibly indicating the settling of the precipitate to the bottom of the tube. The final percent transmission of the 4 fold dilution is the smallest (1.2%), followed by the 16 fold (7.6%), 2 fold (4.1%), 32 fold (6.7%) and 8 fold (7.6%), respectively.

For the solutions containing 1.5% ZLC powder in shower gel, all of the dilutions have a net increase in percent transmission during a 20 minute measurement period. All of the solutions are turbid from the very beginning. The 8 fold dilution has the lowest initial percent transmission at 0.15% transmission. The 16× dilution only slightly increases during the measurement period: from 1.2% to 2.2%. The 2 fold and 32 fold dilutions have a sharp drop in percent transmission at around 1 minute and then continue to increase for the rest of the time. This could be due to the settling of the precipitate. The 4 fold dilution steadily increases during the time period from 6.2% to 8.4%. Overall, the final % transmission is lowest for the 8 fold dilution (1.4%), followed by the 16 fold dilution (2.3%), the 4 fold dilution (8.4%), 32 fold dilution (9.0%) and finally the 2 fold dilution (10.2%), respectively.

For the solutions containing 5% ZLC solution in shower gel, all of the solutions are turbid from the very beginning. The 8 fold dilution as the lowest initial percent transmission at 0.15% transmission and stays relatively stable during the 20 minute measurement period. The 32 fold dilution also stays relatively stable during the measurement period at around 4.9%-5.0%. The 4 fold dilution slowly increases from 5.8% to 8.4%. The 2 fold dilution has a sharp increase initially and then steadily increases to 11.9%. Lastly, the 16 fold dilution has the greatest initial and final % transmission. The 16 fold dilution has a slight dip at around 1 minute to 12.3% but then increases to 15.2% by the end of the measurement period. There are no overlaps among the % transmission of the diluted samples.

For the solutions containing 5% ZLC solution in shower gel, all of the solutions are turbid from the very beginning. The 8 fold dilution as the lowest initial percent transmission at 0.15% transmission and stays relatively stable during the 20 minute measurement period. The 32 fold dilution also stays relatively stable during the measurement period at around 4.9%-5.0%. The 4 fold dilution slowly increases from 5.8% to 8.4%. The 2 fold dilution has a sharp increase initially and then steadily increases to 11.9%. Lastly, the 16 fold dilution has the greatest initial and final % transmission. The 16 fold dilution has a slight dip at around 1 minute to 12.3% but then increases to 15.2% by the end of the measurement period. There are no overlaps among the % transmission of the diluted samples.

In comparison to the control shower gel Sample P0 (containing 0% ZLC), the zinc deposition test clearly shows significant deposition of ZnO nano particles on the surface of ZLC treated side.

The minimum amount of ZLC that still leaves a zinc deposit is determined to be 5% ZLC solution and 1.5% ZLC powder. These contain 0.37% and 0.36% Zn, respectively. It is difficult to see the zinc oxide formed from the turbidity study due to the nature of the shower gel. The original shower gel is already very turbid, whereas ZLC solution is clear. When the ZLC solution was added to the shower gel, a substantial decrease in % transmission is not obvious because the added clarity of the ZLC solution balances out the cloudiness of the newly formed precipitate. For the ZLC powder, a significant decrease in % transmission of the 16× and 32× dilutions is observed. This indicates the precipitation of ZnO for 1.5% ZLC powder in shower gel.

When the skin comes in contact with ZLC solution or powder, ZLC molecules are deposited on the skin surface. During the rinsing process in DI water, ZLC forms ZnO which directly deposits on the surface.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

What is claimed is:

1. A personal cleansing composition comprising
   a) a skin cleansing effective amount of a surfactant, and
   b) a zinc X halide complex present in an amount to provide at least 0.36 weight % of the composition of zinc,
   wherein X is an amino acid or trimethylglycine;
   wherein upon rinsing the skin, the composition deposits a zinc precipitate which provides an SPF factor of at least 2 to skin after washing skin with the personal cleansing composition.

2. The personal cleansing composition of claim 1, wherein the cleansing composition is a liquid cleansing composition.

3. The personal cleansing composition according to claim 1, wherein the zinc X halide complex is formed from precursors, wherein the precursors are a zinc ion source, an X source, and a halide source, wherein the halide source can be part of the zinc ion source, the X source, or a halogen acid.

4. The personal cleansing composition according to claim 3, wherein the zinc ion source is at least one of zinc oxide, zinc chloride, tetrabasic zinc chloride, zinc carbonate, zinc nitrate, zinc citrate, and zinc phosphate.

5. The personal cleansing composition according to claim 3, wherein the X source is at least one of a basic amino acid, lysine, arginine, glycine, and trimethylglycine.

6. The personal cleansing composition according to claim 1 wherein the zinc X halide complex is made by combining zinc oxide with an amino acid hydrohalide.

7. The personal cleansing composition according to claim 1, wherein the zinc X halide complex is made by combining tetrabasic zinc chloride (TBZC) with an amino acid hydrohalide, an amino acid, or trimethylglycine.

8. The personal cleansing composition according to claim 1, wherein the zinc X halide complex has the formula $ZnX_2Hal_2$ or $ZnX_3Hal_2$, wherein Zn is a divalent zinc ion and Hal is a halide ion.

9. The personal cleansing composition according to claim 1, wherein a total amount of zinc present in the composition is 0.36 to 10 weight %.

10. The personal cleansing composition according to claim 1, wherein the zinc X halide complex is present in an amount of 1.5 to 40% by weight of the composition.

11. The personal cleansing composition according to claim 1, wherein a molar ratio of zinc to X in the zinc X halide complex is 2:1 to 1:4.

12. The personal cleansing composition according to claim 1 wherein the halide is chloride.

13. The personal cleansing composition according to claim 1 wherein the zinc X halide complex is zinc lysine chloride complex.

14. The personal cleansing composition according to claim 1 wherein the zinc X halide complex is $ZnLysine_2Cl_2$ or $ZnLysine_3Cl_2$ complex.

15. The personal cleansing composition according to claim 1, wherein the composition provides an SPF factor of 2 to 45 to skin after washing skin with the personal cleansing composition.

16. The personal cleansing composition according to claim 1 wherein the composition is a body wash or shower gel.

17. A method of reducing sun damage to the skin or protecting the skin from sunburn or sun damage, comprising washing the skin with the liquid cleansing composition of claim 1 prior to exposure to the sun.

18. A method of killing bacteria comprising contacting the bacteria with the composition of claim 1.

19. A method of reducing perspiration comprising washing skin with the composition of claim 1.

* * * * *

UNITED STATES PATENT AND TRADEMARK OFFICE
CERTIFICATE OF CORRECTION

PATENT NO. : 10,188,112 B2
APPLICATION NO. : 14/650952
DATED : January 29, 2019
INVENTOR(S) : Hardy et al.

Page 1 of 2

It is certified that error appears in the above-identified patent and that said Letters Patent is hereby corrected as shown below:

On the Title Page

Item (63):
"Continuation-in-part of application No. PCT/US2012/070489, filed on Dec. 19, 2012, which is a continuation-in-part of application No. PCT/US2012/070492, filed on Dec. 19, 2012, which is a continuation-in-part of application No. PCT/US2012/070498, filed on Dec. 19, 2012, which is a continuation-in-part of application No. PCT/US2012/070501, filed on Dec. 19, 2012, which is a continuation-in-part of application No. PCT/US2012/070505, filed on Dec. 19, 2012, which is a continuation-in-part of application No. PCT/US2012/070506, filed on Dec. 19, 2012, which is a continuation-in-part of application No. PCT/US2012/070513, filed on Dec. 19, 2012, which is a continuation-in-part of application No. PCT/US2012/070521, filed on Dec. 19, 2012, which is a continuation-in-part of application No. PCT/US2012/070525, filed on Dec. 19, 2012, which is a continuation-in-part of application No. PCT/US2012/070534, filed on Dec. 19, 2012, which is a continuation-in-part of application No. PCT/US2012/070537, filed on Dec. 19, 2012, said application No. PCT/US2013/070932 is a continuation-in-part of application No. PCT/US2013/046268, filed on Jun.18, 2013, and a continuation-in-part of application No. PCT/US2013/050845, filed on Jul. 17, 2013, and a continuation-in-part of application No. PCT/US2013/068852, filed on Nov. 7, 2013, which is a continuation-in-part of application No. PCT/US2013/068860, filed on Nov. 7, 2013, said application No. PCT/US2013/070932 is a continuation-in-part of application No. PCT/US2013/068859, filed on Nov. 7, 2013, and a continuation-in-part of application No. PCT/US2013/068854, filed on Nov. 7, 2013."

Should be changed to:
—Continuation-in-part of application No. PCT/US2012/070489, filed on Dec. 19, 2012, and a continuation-in-part of application No. PCT/US2012/070492, filed on Dec. 19, 2012, and a continuation-in-part of application No. PCT/US2012/070498, filed on Dec. 19, 2012, and a continuation-in-part of application No. PCT/US2012/070501, filed on Dec. 19, 2012, and a continuation-in-part of application No. PCT/US2012/070506, filed on Dec. 19, 2012, and a continuation-in-part of application No. PCT/US2012/070521, filed on Dec. 19, 2012, and a continuation-in-part of application No. PCT/US2012/070525, filed on Dec. 19, 2012, and a Signed and Sealed this
Seventeenth Day of September, 2019

Andrei Iancu
*Director of the United States Patent and Trademark Office*

CERTIFICATE OF CORRECTION (continued)
U.S. Pat. No. 10,188,112 B2 continuation-in-part of application No. PCT/US2012/070534, filed on Dec. 19, 2012, and a continuation-in-part of application No. PCT/US2012/070537, filed on Dec. 19, 2012, and a continuation-in-part of application No. PCT/US2013/046268, filed on Jun. 18, 2013, and a continuation-in-part of application No. PCT/US2013/050845, filed on Jul. 17, 2013, and a continuation-in-part of application No. PCT/US2013/068852, filed on Nov. 7, 2013, and a continuation-in-part of application No. PCT/US2013/068860, filed on Nov. 7, 2013, and a continuation-in-part of application No. PCT/US2013/068859, filed on Nov. 7, 2013, and a continuation-in-part of application No. PCT/US2013/068854, filed on Nov. 7, 2013, and said application No. PCT/US2013/068852 is a continuation-in-part of application No. PCT/US2012/070505, filed on Dec. 19, 2012, and a continuation-in-part of application No. PCT/US2012/070513, filed on Dec. 19, 2012.—